US00PP21160P2

(12) United States Plant Patent
Koning

(10) Patent No.: US PP21,160 P2
(45) Date of Patent: Jul. 13, 2010

(54) ***RHODODENDRON* PLANT NAMED 'FUJI'**

(50) Latin Name: ***Rhododendron simsii*×*Rhododendron linearifolia***
Varietal Denomination: Fuji

(76) Inventor: Lammert Koning, Lietsweg 4, 9364 TB Nuis (NL)

( * ) Notice: Subject to any disclaimer, the term of this patent is extended or adjusted under 35 U.S.C. 154(b) by 0 days.

(21) Appl. No.: 12/386,657

(22) Filed: Apr. 20, 2009

(51) Int. Cl.
*A01H 5/00* (2006.01)

(52) U.S. Cl. ..... Plt./240

(58) Field of Classification Search ..... Plt./240
See application file for complete search history.

*Primary Examiner*—Annette H Para
(74) *Attorney, Agent, or Firm*—C. A. Whealy

(57) ABSTRACT

A new and distinct cultivar of *Rhododendron* plant named 'Fuji', characterized by its upright to outwardly spreading plant habit; freely branching habit; lanceolate-shaped leaves; freely flowering habit; single dark pink-colored flowers with lanceolate-shaped petals; and good postproduction longevity.

2 Drawing Sheets

Botanical designation: *Rhododendron simsii*×*Rhododendron linearifolia.*
Cultivar denomination: 'Fuji'.

BACKGROUND OF THE INVENTION

The present Invention relates to a new and distinct cultivar of *Rhododendron* plant, botanically known as *Rhododendron simsii*×*Rhododendron linearifolia*, and hereinafter referred to by the name 'Fuji'.

The new *Rhododendron* plant is a product of a planned breeding program conducted by the Inventor in Paterswolde, The Netherlands. The objective of the breeding program is to create new *Rhododendron* varieties having unique and attractive leaf and flower forms.

The new *Rhododendron* plant originated from a cross-pollination made by the Inventor in April, 2001, in Paterswolde, The Netherlands, of

*Rhododendron simsii* 'Terra Nova', not patented, as the female, or seed, parent with an unnamed proprietary selection of *Rhododendron linearifolia*, not patented, as the male, or pollen, parent. The new *Rhododendron* was discovered and selected by the Inventor as a single flowering plant within the progeny of the stated cross-pollination in a controlled greenhouse environment in Paterswolde, The Netherlands in 2003.

Asexual reproduction of the new *Rhododendron* plant by terminal cuttings taken in a controlled environment in Paterswolde, The Netherlands since 2004 has shown that the unique features of this new *Rhododendron* plant are stable and reproduced true to type in successive generations.

SUMMARY OF THE INVENTION

Plants of the new *Rhododendron* have not been observed under all possible environmental conditions. The phenotype may vary somewhat with variations in environment such as temperature, daylength and/or light intensity without, however, any variance in genotype. The following traits have been repeatedly observed and are determined to be the unique characteristics of 'Fuji'. These characteristics in combination distinguish 'Fuji' as a new and distinct cultivar:

1. Upright to outwardly spreading plant habit.
2. Freely branching habit.
3. Lanceolate-shaped leaves.
4. Freely flowering habit.
5. Single dark pink-colored flowers with lanceolate-shaped petals.
6. Good postproduction longevity.

Plants of the new *Rhododendron* differ from plants of the female parent, 'Terra Nova', in the following characteristics:

1. Plants of the new *Rhododendron* have lanceolate-shaped leaves whereas plants of 'Terra Nova' have oval-shaped leaves.
2. Plants of the new *Rhododendron* have pubescent leaves whereas plants of 'Terra Nova' have glabrous leaves.
3. Flowers of plants of the new *Rhododendron* have lanceolate-shaped petals whereas flowers of plants of 'Terra Nova' have spatulate-shaped petals.

Plants of the new *Rhododendron* differ from plants of the male parent selection in the following characteristics:

1. Plants of the new *Rhododendron* are more compact than plants of the male parent selection.
2. Flowers of plants of the new *Rhododendron* have longer petals than flowers of plants of the male parent selection.

Plants of the new *Rhododendron* can be compared to the plants of *Rhododendron simsii* 'Miss Lulu', disclosed in U.S. Plant Pat. No. 14,263. In side-by-side comparisons conducted in Paterswolde, The Netherlands, plants of the new *Rhododendron* differed from plants of 'Miss Lulu' in the following characteristics:

1. Plants of the new *Rhododendron* had lanceolate-shaped leaves whereas plants of 'Miss Lulu' had elliptic-shaped leaves.
2. Plants of the new *Rhododendron* had single flowers whereas plants of 'Miss Lulu' had double flowers.
3. Flowers of plants of the new *Rhododendron* had lanceolate-shaped petals whereas flowers of plants of 'Miss Lulu' had obovate-shaped petals.

BRIEF DESCRIPTION OF THE PHOTOGRAPHS

The accompanying colored photographs illustrate the overall appearance of the new *Rhododendron* plant.

These photographs show the colors as true as it is reasonably possible to obtain in colored reproductions of this type.

Colors in the photographs may differ slightly from the color values cited in the detailed botanical description, which accurately describe the colors of the new *Rhododendron* plant.

The photograph on the first sheet comprises a side perspective view of typical flowering plants of 'Fuji' grown in a container.

The photograph at the top of the second sheet is a close-up view of typical flowers of 'Fuji'.

The photograph at the bottom of the second sheet is a close-up view of typical leaves of 'Fuji'.

DETAILED BOTANICAL DESCRIPTION

The aforementioned photographs and following observations and measurements describe plants grown in Aalsmeer, The Netherlands in one-liter containers with three plants per container. Plants were grown in a glass-covered greenhouse during the winter and under commercial *Rhododendron* production conditions. During the production of the plants, day temperatures ranged from 16° C. to 30° C. and night temperatures ranged from 10° C. to 18° C. Plants used for the photographs and description were 18 months old and were pinched one time. In the following description, color references are made to The Royal Horticultural Society Colour Chart, Fifth Edition, except where general terms of ordinary dictionary significance are used.

Botanical classification: *Rhododendron simsii*×*Rhododendron linearifolia* 'Fuji'.

Parentage:

*Female, or seed, parent.*—*Rhododendron simsii* 'Terra Nova', not patented.

*Male, or pollen, parent.*—Unnamed proprietary selection of *Rhododendron linearifolia*, not patented.

Propagation:

*Type.*—By terminal vegetative cuttings.

*Time to initiate roots.*—About 45 days at soil temperatures of 18° C. to 20° C.

*Time to produce a rooted young plant.*—About 90 days at soil temperatures of 18° C. to 20° C.

*Root description.*—Fine, fibrous; brownish in color.

*Rooting habit.*—Freely branching; dense.

Plant description:

*Plant form and growth habit.*—Perennial, evergreen; upright to outwardly spreading plant habit; broad inverted triangle; moderately vigorous to low vigor; full and bushy plants; freely flowering habit with numerous single flowers per plant.

*Branching habit.*—Freely branching habit; about 14 lateral branches develop per plant; pinching enhances lateral branch development. Plant height, soil level to top of flowers: About 15.3 cm.

*Plant diameter, area of spread.*—About 25.5 cm.

*Lateral branch description.*—Length: About 5.8 cm. Diameter: About 2 mm. Internode length: About 7.5 mm. Strength: Strong. Texture, developing: Pubescent. Texture, mature: Woody. Color, developing: Close to 145A. Color, mature: Close to 165B to 165C.

*Foliage description.*—Arrangement: Alternate, single. Length: About 4.5 cm. Width: About 7.5 mm. Shape: Lanceolate. Apex: Acute. Base: Attenuate. Margin: Entire; undulate. Venation pattern: Pinnate. Texture, upper and lower surfaces: Pubescent; rugose. Color: Developing leaves, upper surface: Between N137A and 147A. Developing leaves, lower surface: Close to 147B. Fully expanded leaves, upper surface: Between N137A and 147A; venation, close to 146C to 146D. Fully expanded leaves, lower surface: Close to 137A to 137B; venation, close to 147C to 147D.

*Petiole.*—Length: About 6 mm. Diameter: About 1.5 mm. Texture, upper and lower surfaces: Pubescent. Color, upper and lower surfaces: Close to 147C.

Flower description:

*Natural flowering season.*—Plants of the new *Rhododendron* typically flower from the late winter to early summer in The Netherlands.

*Flower arrangement and appearance.*—Single "spider-shaped" flowers arranged in terminal clusters; freely flowering habit with usually about seven flowers developing per terminal branch; flowers face upward or outward.

*Postproduction longevity.*—Good postproduction longevity; plants maintain good flower substance for about two weeks on the plant; flowers not persistent.

*Fragrance.*—Faint; sweet and pleasant.

*Flower diameter.*—About 5.2 cm.

*Flower depth.*—About 3.4 cm.

*Flower bud* (*before showing color*).—Length: About 1 cm. Diameter: About 7 mm. Shape: Broadly ovate. Color: Close to 143C.

*Petals.*—Arrangement: Single flower form with five petals arranged in a single whorl. Length: About 3.9 cm. Width: About 5 mm. Shape: Lanceolate. Apex: Acute. Margin: Entire. Texture, upper and lower surfaces: Smooth, glabrous; somewhat velvety. Color: When opening, upper surface: Between 67B and 68A; towards the base, close to 68B. When opening, lower surface: Close to 67C. Fully opened, upper surface: Close to 71D; towards the base, close to 68B; color does not fade with development. Fully opened, lower surface: Close to 71C to 71D.

*Sepals.*—None observed.

*Peduncles.*—Length: About 3 mm. Diameter: About 1.5 mm. Angle: About 15° from vertical. Strength: Moderately strong. Texture: Pubescent. Color: Close to 144A.

*Reproductive organs.*—Androecium: Quantity per flower: About five. Filament length: About 2.9 cm. Filament color: Close to 71D; towards the base, close to 68C. Anther length: About 2 mm. Anther color: Close to 173D. Pollen amount: Scarce. Pollen color: Close to 155D. Gynoecium: Quantity per flower: Typically one. Pistil length: About 5 mm. Style length: About 4 mm. Style color: Close to 146B to 146C tinged with close to 53D. Stigma shape: Club-shaped; towards the apex, flattened. Stigma color: Close to 143A. Ovary color: Close to 147A.

*Seed/fruit.*—Seed and fruit development have not been observed.

Weather/temperature tolerance: Plants of the new *Rhododendron* have been observed to be tolerant to rain and wind and to tolerate temperatures from about −10° C. to about 35° C.

Disease/pest resistance: Plants have not been observed to be resistant to pathogens and pests common to *Rhododendrons*.

It is claimed:

1. A new and distinct cultivar of *Rhododendron* plant named 'Fuji' as illustrated and described.

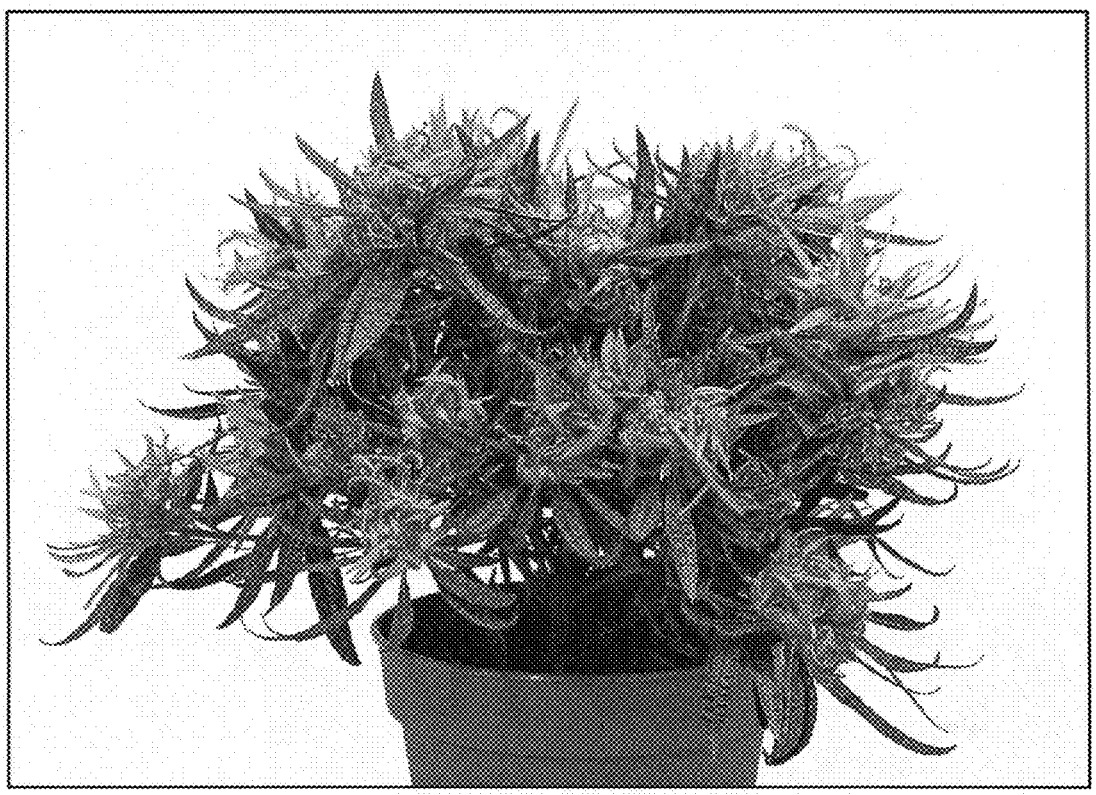

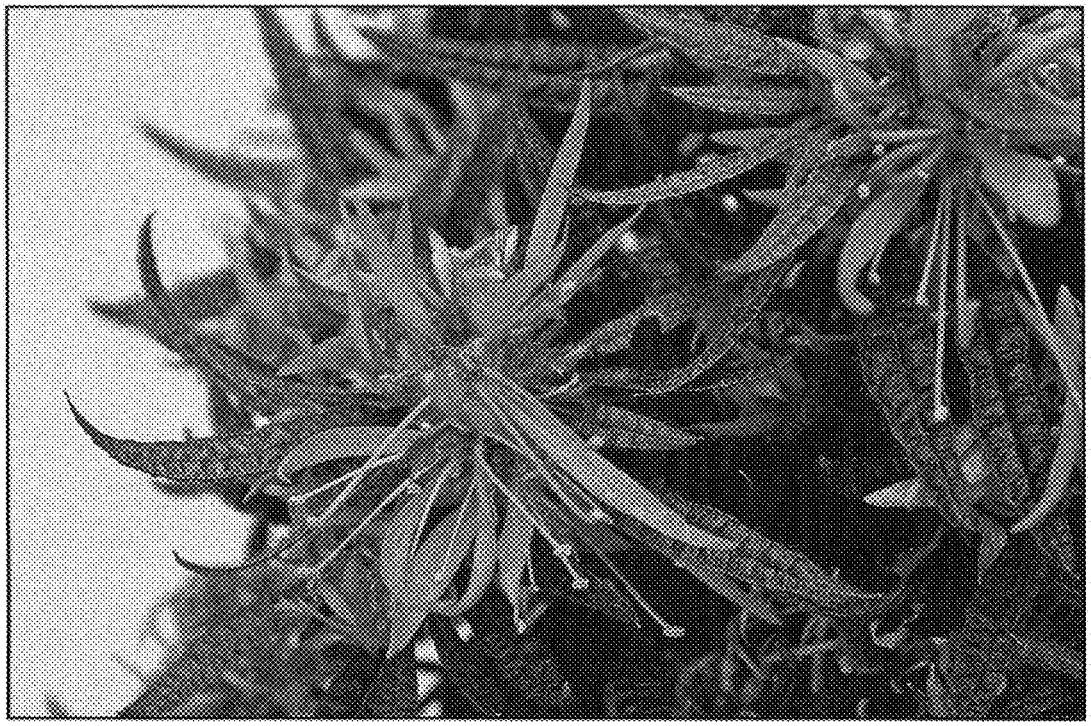
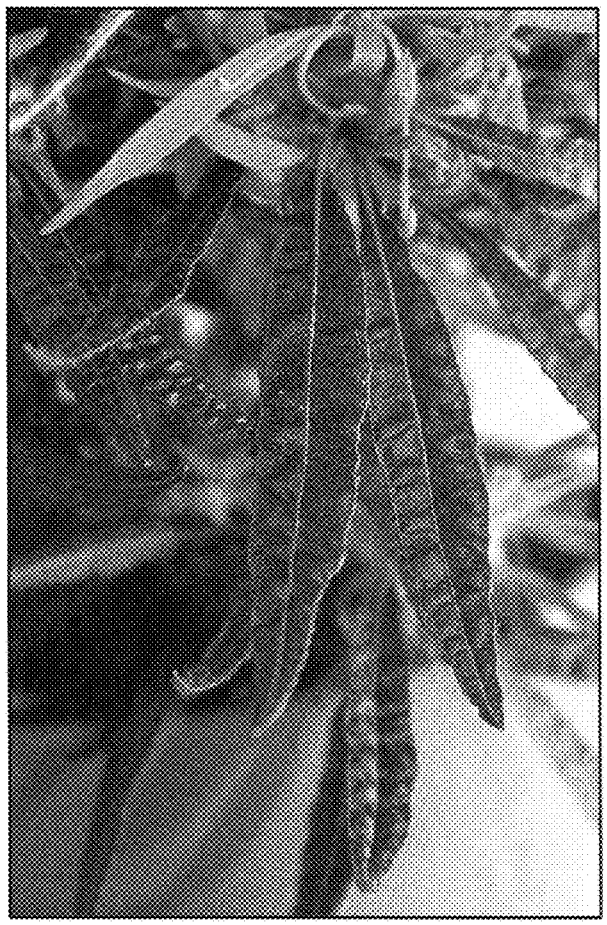

* * * * *